United States Patent [19]

Blakeley et al.

[11] Patent Number: 5,038,785
[45] Date of Patent: Aug. 13, 1991

[54] CARDIAC AND RESPIRATORY MONITOR WITH MAGNETIC GRADIENT NOISE ELIMINATION

[75] Inventors: Douglas M. Blakeley; Raymond E. Gangarosa, both of Euclid, Ohio

[73] Assignee: Picker International, Inc., Highland Hts., Ohio

[21] Appl. No.: 546,253

[22] Filed: Jun. 29, 1990

Related U.S. Application Data

[63] Continuation of Ser. No. 98,546, Sep. 18, 1987, abandoned, Continuation-in-part of Ser. No. 764,440, Aug. 9, 1985, Pat. No. 4,694,837.

[51] Int. Cl.[5] ............................................. A61B 5/055
[52] U.S. Cl. .............................. 128/653 A; 128/653 R; 128/671; 128/696; 128/901
[58] Field of Search ............. 128/653 A, 653 SC, 696, 128/687, 708, 716, 731, 901

[56] References Cited

U.S. PATENT DOCUMENTS

| | | | |
|---|---|---|---|
| 3,848,586 | 11/1974 | Suzuki et al. | 128/696 |
| 4,005,701 | 2/1977 | Aisenberg et al. | 128/901 |
| 4,478,224 | 10/1984 | Bailey | 128/708 |
| 4,694,837 | 9/1987 | Blakeley et al. | 128/653 |

Primary Examiner—Ruth S. Smith
Attorney, Agent, or Firm—Fay, Sharpe, Beall, Fagan, Minnich & McKee

[57] ABSTRACT

A magnetic resonance imaging apparatus (A) generates a uniform magnetic field, causes gradient fields transversely thereacross, excites resonance in nuclei within the image region, receives radio frequency signals from resonating nuclei, and reconstructs images representative thereof. Electrodes (30) monitor the cardiac cycle of a patient (B) being imaged and an expansion belt (32) monitors the respiratory cycle. During a magnetic resonance imaging scan, noise signal wave forms or spikes are superimposed on the cardiac cycle signal. A noise spike detector detects noise spikes. Specifically, a comparator (48) compares each wave form received from the electrodes with properties of a cardiac signal, such as the slope. When the comparator determines that a noise wave form is being received, it gates a track and hold circuit (52). The track and hold circuit passes the received signal except when gated by the comparator. When gated by the comparator, the track and hold circuit continues to supply the same output amplitude as it had in the beginning of the gating period. A filter (54) smooths the plateaus in the cardiac signal formed as the noise signal wave forms are removed.

7 Claims, 4 Drawing Sheets

CARDIAC AND RESPIRATORY MONITOR WITH MAGNETIC GRADIENT NOISE ELIMINATION

This application is a continuation of U.S. patent application Ser. No. 098,546, now abandoned, filed Sept. 18, 1987, which is a continuation-in-part of U.S. application Ser. No. 764,440, filed Aug. 9, 1985, now U.S. Pat. No. 4,694,837.

BACKGROUND OF THE INVENTION

The present invention relates to the electronic, anatomical examination arts. More particularly, it relates to the gating and control of patient imaging in conjunction with body motion of the patient. Particular application is found in conjunction with cardiac and respiratory gating of magnetic resonance imaging and the invention will be described with particular reference thereto. However, it is to be appreciated that the invention may have other applications in other electronic imaging fields and in conjunction with monitoring other anatomical motion.

Heretofore, magnetic resonance images have commonly been constructed from about 256 views, each view requiring about 200–1000 milliseconds to acquire. When imaging through the patient's chest or abdomen, the images tend to become blurred or degraded by cardiac and respiratory motion.

Various cardiac and respiratory monitors have been utilized in computerized tomography and other imaging systems. For sensing cardiac function, conductive wires or leads commonly carried cardiac signals from the patient adjacent the imaging zone to a remotely located signal processing circuit. In magnetic resonance imaging, conducting leads extending into the imaging zone cause significant degradation of the acquired image. The degradation is a result of penetration of the RF barrier by conducting wire which conveys RF noise present in the atmosphere into the imaging area. In all patient monitoring devices, high current and voltage isolation devices are necessary to protect the patients from hazardous shocks. Fiber optic conductors, for example, convey sensed cardiac monitor signals without the risk of patient shock and maintain the RF integrity of the imaging system.

In magnetic resonance imaging apparatus, relatively strong gradient magnetic fields are applied during acquisition of each view. These changing magnetic fields induce stray currents in electronic circuitry associated with cardiac monitoring adjacent the imaging zone. These induced currents tend to interfere with the cardiac monitoring function and signals indicative thereof. In particular, the changing gradient fields tend to generate voltage spikes which are similar in appearance to the signals which represent a cardiac R-wave in the cardiac electrocardiogram (ECG) cycle. Because many cardiac monitors key on the R-wave portion, these gradient magnetic field changes tend to produce false cardiac signals. However, the noise spikes, tend to differ from the R-wave and other cardiac waveform in several respects, such as shorter duration and rise time, stepper slope, higher amplitude, and the like.

The present invention contemplates a new and improved anatomical gating system which overcomes the above referenced problems and others.

SUMMARY OF THE INVENTION

In accordance with one aspect of the present invention, a magnetic resonance imaging apparatus is provided in which at least one anatomical condition is monitored. An anatomical condition detector is disposed adjacent an image region for monitoring a first anatomical condition and producing a first electrical signal which varies in accordance with the monitored condition. The first electrical signal has properties, such as slope, amplitude, shape, and the like, which are predictable from an a priori knowledge of the monitored physiological condition. A magnetic field generating means generates a magnetic field through the image region. A gradient field means generates magnetic field gradients across the image region to phase encode resonating nuclei therein. The gradient magnetic fields induce noise wave forms or spikes which are superimposed on the first electrical signal. A radio frequency excitation means selectively applies radio frequency pulses to the image region to excite magnetic resonance. The excitation pulses again induce noise which is superimposed on the first electrical signal. A receiving means receives the resonance signals which are reconstructed by an image reconstruction means into an image representation. A comparing means compares the first electrical signal with a preselected signal property. Under control of the comparing means, a separating means separates the noise and first signal.

In accordance with another aspect of the present invention, an anatomical monitor is provided which is particularly adapted for use in environments in which noise signals are induced. A monitoring means converts a monitored anatomical condition into an electrical signal indicative thereof. The anatomical condition signal has properties and characteristics that are predictable from the nature of the monitored anatomical condition. The electrical signal may have noise waveform that are distinguishable from the anatomical signal superimposed thereon. A separating means selectively separates the superimposed noise and anatomical condition signals. More specifically, the separating means deletes noise contaminated portions of the superimposed signal and replaces them with signals derived from adjoining noise-free anatomical signal portions.

In accordance with another aspect of the present invention, a cardiac detector is provided which is disposed adjacent an image region of a magnetic scanner. A cardiac monitoring means monitors a cardiac cycle of the patient and produces a cardiac signal indicative thereof. The cardiac signal conforms generally to a characteristic cardiac wave form. Changing electromagnetic fields of the scanner induce electrical noise signals that are superimposed on the cardiac signal. A noise signal detecting means detects noise signal waveform. A separating means that is operatively connected with the noise signal detecting means separates the cardiac and noise signals.

One advantage of the present invention is that it enables anatomical condition monitoring to continue during a magnetic resonance scan.

Another advantage of the present invention is that it facilitates cardiac imaging in which scans are triggered in response to a cardiac monitor in order to image a selected phase of the cardiac cycle.

Another advantage of the present invention is that it eliminates and suppresses electrical interference which is caused by electromagnetic field changes.

Still further advantages of the present invention will become apparent to those of ordinary skill in the art upon reading and understanding the following detailed description of the preferred embodiment.

BRIEF DESCRIPTION OF THE DRAWINGS

The present invention may take form in various parts and arrangements of parts or in various steps and arrangements of steps. The drawings and pictured components are only for purposes of illustrating a preferred embodiment and are not to be construed as limiting the invention.

DETAILED DESCRIPTION OF THE PREFERRED EMBODIMENT

Figure 1:
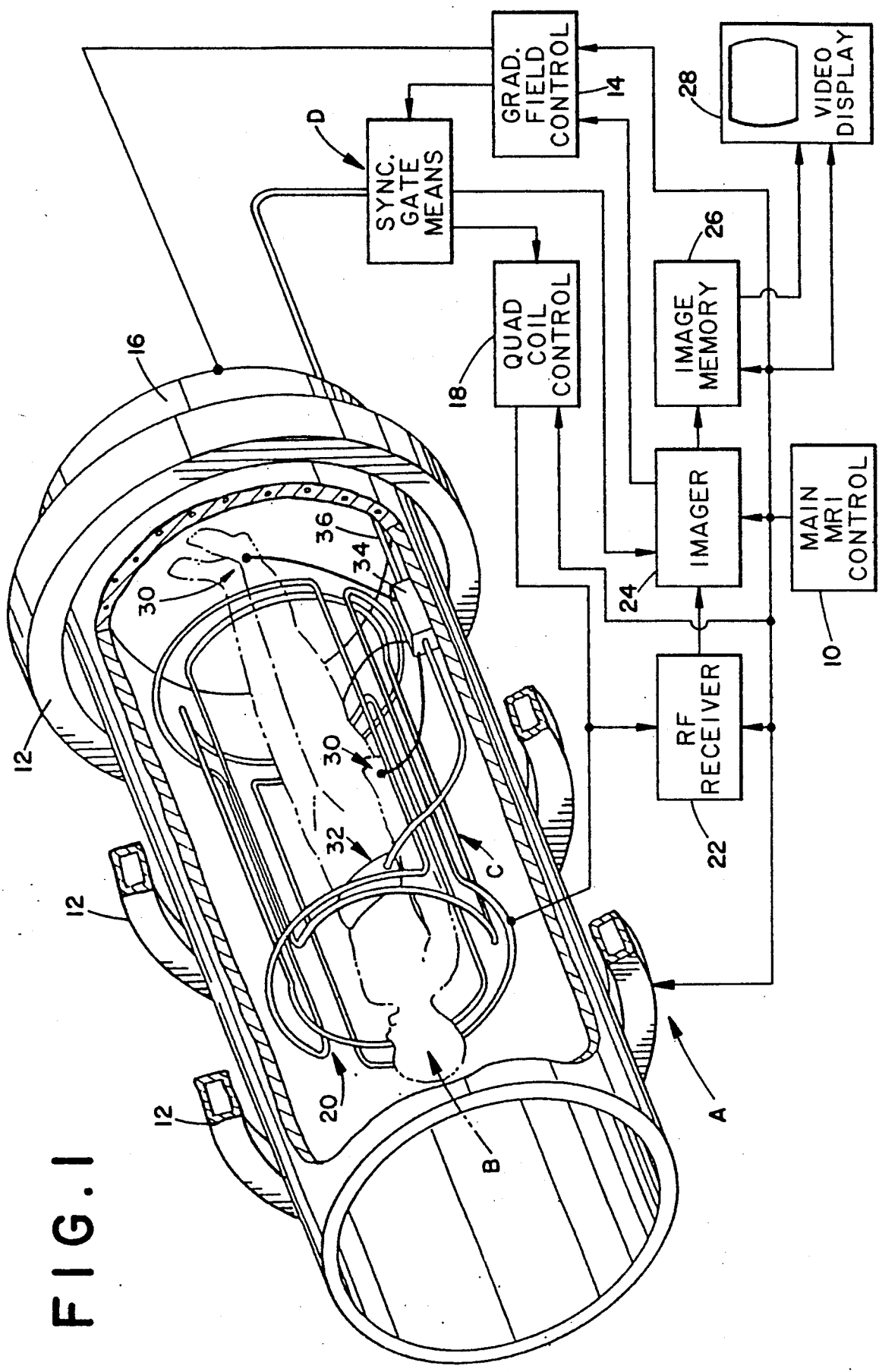
FIG. 1 is a diagrammatic illustration of a magnetic resonance imaging apparatus incorporating the present invention.

With reference to FIG. 1, a magnetic resonance imaging apparatus A receives a patient B of whom an image is to be generated. An anatomical monitoring means C is disposed adjacent the patient within the magnetic resonance imaging apparatus to monitor anatomical conditions of the patient. A synchronizing means D receives optically encoded signals from the anatomical monitoring means C and gates the magnetic resonance imaging apparatus A in accordance therewith.

The magnetic resonance imaging apparatus A includes main controller 10 which directs each of the following subsystems. An MRI magnet 12 generates a strong, uniform magnet field longitudinally along the image region. A gradient field control 14 causes a gradient coil 16 to generate magnetic field gradients in the image region at selected angular orientations. A quadrature coil control means 18 causes quadrature coils 20 to excite magnetic resonance of selected nuclei in the image region and to receive radio frequency resonance signals therefrom. Received radio frequency resonance signals are conditioned by a radio frequency receiver 22 and processed by an imager 24 to produce data indicative of an image of a selected region of the patient. The image data are stored and accumulated in an image memory 26. A display means 28, such as a video monitor, produces a man-readable display of the imaged data.

The patient monitor means C includes a first anatomical condition detector, in the preferred embodiment electrodes 30, for monitoring the patient's cardiac cycle and generating an electrocardiogram signal indicative thereof. The electrodes are attached to the patient in a known manner. A second anatomical condition detector monitors a second anatomical condition of the patient; particularly, a respiratory cycle monitoring means 32 monitors the patient's respiratory cycle. In the preferred embodiment, the respiratory monitor is an air filled elastomeric belt which expands and contracts with the patient's breathing. The expansion and contraction causes corresponding changes in the air pressure that are converted to electrical signals which are indicative of the patient's respiratory cycle.

Figure 2:
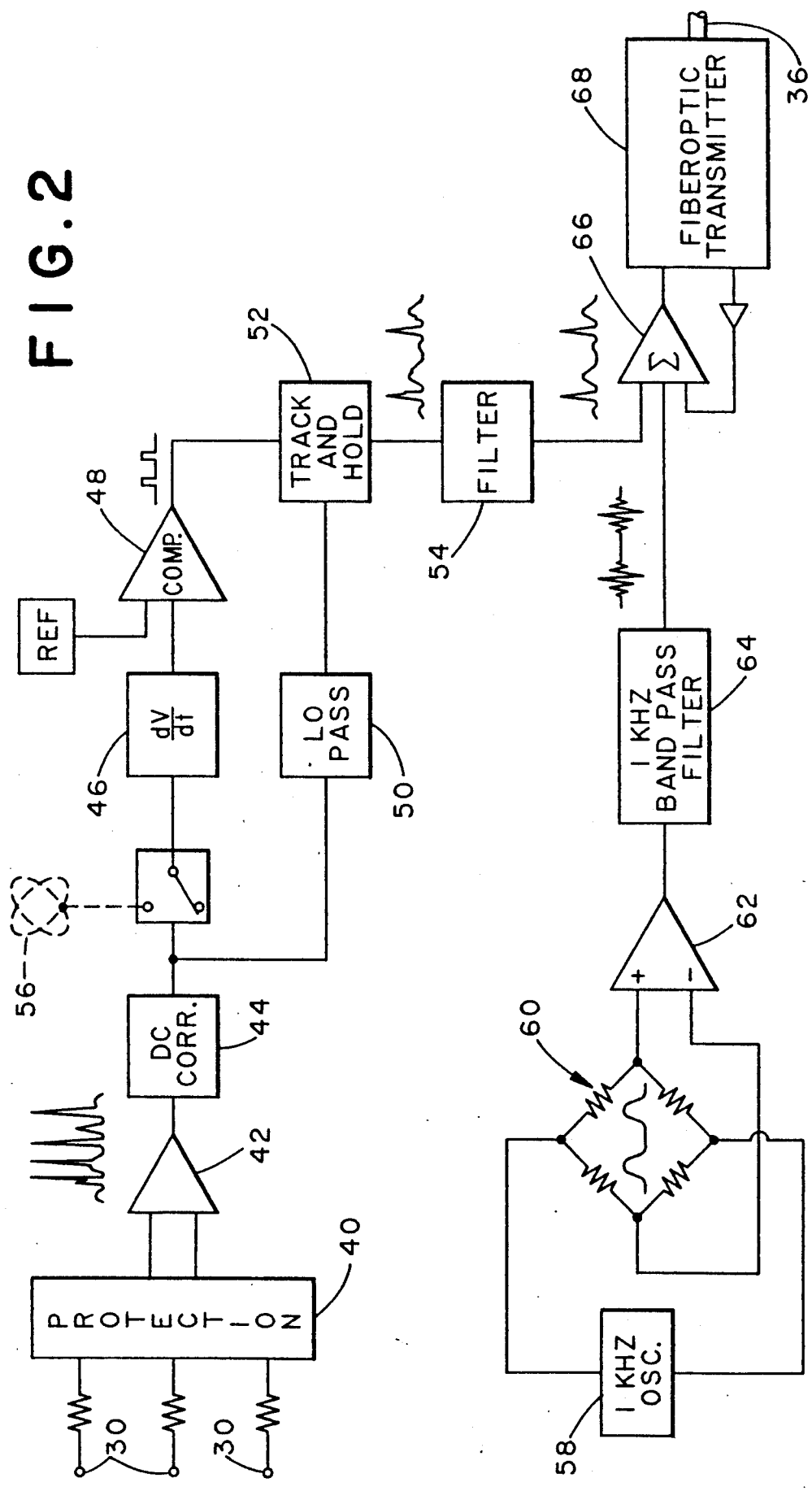
FIG. 2 is a circuit diagram of a patient monitoring and light signal transmitting portion of the present invention.

A patient monitor circuit 34, which is illustrated in greater detail in FIG. 2, amplifies and processes the monitored cardiac and respiratory cycle data and produces a light signal which is encoded in accordance with both the monitored cardiac and respiratory conditions. The patient monitor circuit 34 is disposed adjacent the patient and within the magnetic field. A wave guide 36, preferably a fiber optic, acoustic, sonic, or other non-electrical wave guide conveys the cardiac, respiratory, or other anatomical data from the high magnetic field region. Optionally, telemetry techniques which are not affected by electromagnetic radiation, such as infrared telemetry, may be utilized directly without a wave guide.

The gating means D causes the quadrature coil control means 18 to initiate a magnetic resonance view a preselected duration after each R-wave peak of the electrocardiogram cycle. The duration after the R-wave peak is selected to permit imaging at a selected portion of the cardiac cycle. The gating means further blocks the processing of data from the portions of the respiratory cycle in which respiratory movement is greatest. The processing of data is enabled during the most quiescent portions of the respiratory cycle. The blocking and enabling of data processing may be achieved by enabling and disabling operation of the quadrature coil control means 18, by enabling and disabling the imager 24, or controlling other control functions from the MRI magnetic resonance imaging controller 10.

In one mode of operation, the gradient field controller 14 is connected with the gating means D to prevent the initiation of a scan while the gradient field is being applied. The gradient field may cause generation of noise signals which are confusingly similar to electrocardiogram R-wave signals. Blocking initiation of a scan while the gradient field is applied prevents the moving gradient field related noise from inappropriately triggering a scan.

With reference to FIG. 2, the cardiac monitoring electrodes 30 are connected with a protection circuit 40 which protects the electronics in the unlikely event of defibrillation of the patient. The protection circuit also protects the patient from microshock with a high input impedance and filters RF signals sensed by the monitoring electrodes. An amplifier 42 adjusts the magnitude of the first anatomical condition or cardiac signals. A DC correction circuit 44 removes DC offset which is present on most electrocardiograms.

As indicated above, stray noise signal components or wave forms are superimposed on the cardiac signals or other wave forms by the application of magnetic field gradients and RF excitation pulses in the image region. These noise components generally take the form of sharp spikes which rise and fall with a stepper slope than any components of a cardiac signal. Typically, a noise spike has about 1 msec duration compared to 10 msec for an R-wave. A noise detecting means detects the occurance of a characteristic noise waveform or spike. Specific to the embodiment of FIG. 2, a slope or other wave form property measuring means 46, such as a circuit which takes a derivative of the received signal, measures one or more selected properties of each received waveform of the received signal. In the illustrated embodiment, the slope of the leading edge of each waveform is measured. A comparing means 48 compares the slope or other preselected property of the received signal with preselected standards. The standards may be selected from a priori knowledge of the monitored anatomical condition, from trial and error experimentation with each subject, or the like.

Although the slope is illustrated by way of example, it is to be appreciated that other properties may be used instead of or in conjunction with the slope. For example, the comparing means may compare amplitude, characteristic wave shape, proximity of characteristic wave shapes, relative height of characteristic wave shapes, relative duration of characteristic wave shapes, relationship among proximate wave forms, and the like. Based on these comparisons, the comparing means 48 differentiates between the anatomical condition signal and the superimposed noise. The better the selected comparison algorithm, the more accurately and reliably the comparing means can distinguish between the two.

A separating means separates the noise and anatomical condition signals. More specifically, the separating means deletes a noise waveform and the concurrent portion of any underlying anatomical condition signal. The deleted signal portion is replaced with a signal portion interpolated from or otherwise based on the adjacent noise-free anatomical condition signal portions. The separating means includes a low pass filter 50 which removes high frequency components from the combined noise and anatomical condition signals. The low pass filter also functions as a delay means to delay the signal. A track and hold means 52 tracks the filtered signal until it receives a control pulse from the comparing means 48 during which it holds the last value. That is, the track and hold circuit passes the same signal that it receives unless the comparing means 48 determines that a noise signal is about to pass through. To remove the noise, the comparing means causes the track and hold circuit to produce the last amplitude value continuously until the control pulse is removed. In this manner, noise spikes are removed and replaced by relatively flat plateaus. A low pass filter 54 smoothes the output signal to round the flat plateaus caused when the noise spikes were removed substantially back into a smooth cardiac signal. Other interpolation algorithms for deriving substitute waveform portions from accepted anatomical wave form portions may also be utilized.

Optionally, a separate delay means may be provided before the track and hold means 52 such that the control pulses from the comparing means arrive at the track and hold circuit concurrently with the noise spikes. Alternately, the waveform characteristic measuring means 46 may be connected with a source of noise signal components such as an antenna 56. The antenna is disposed such that noise waveforms are concurrently induced in the antenna and the ECG leads. In this manner, the antenna functions as a means for monitoring or detecting the changes in the magnetic field which induce the noise waveforms in the antenna. The antenna may be pair of orthogonal loops, a wire that parallels the ECG leads, or the like. If the antenna were to receive the same noise signal as the ECG leads, the signals could be subtracted. However, locational and orientational differences in the antenna and the leads cause differences at least in the amplitude of their concurrently occuring noise spikes.

As yet another alternative, the noise detecting means may be connected with the cause of the noise, specifically the gradient field control means 14. Characteristic wave form components of the gradient drive signal may be identified by the measuring means 46 as the indicator of noise.

The respiratory sensing belt is connected with a balanced bridge type pressure transducer 58 which produces an electrical signal that varies in amplitude with the respiratory cycle. Commonly, the cardiac cycle is about one second in length and the respiratory cycle is about five to ten seconds in length. Because the cardiac and respiratory cycles are of such similar frequency, there is a tendency for the two signals, if mixed, to become inseparable. To overcome this problem, an audio frequency carrier signal generator 60 applies an audio frequency carrier signal, e.g. one kilohertz, across the balanced bridge pressure transducer. This modulates or encodes the carrier signal in accordance with the second anatomical condition, i.e. the monitored pressure. A beat pattern or amplitude variation carries the encoded respiratory cycle data. In the preferred embodiment, the carrier signal is amplitude modulated. Optionally, frequency modulation or other encoding techniques may be utilized. An amplifier 62 increases the amplitude of the encoded carrier signal. A band pass filter 64 removes distortion and superimposed off frequency signal components.

A signal combining or summing means 66 adds or otherwise combines the cardiac and respiratory signals. A fiber optic transmitter 68, which includes a non-electric signal source such as a light source for generating a light or other non-electrical signal and an encoding means for encoding the light or non-electric signal in accordance with the cardiac and respiratory encoded data. In the preferred embodiment, the frequency of the light signal from the light source is modulated in proportion to the magnitude of the voltage of the combined cardiac and respiratory signals from the signal combining means 66.

Figure 3:
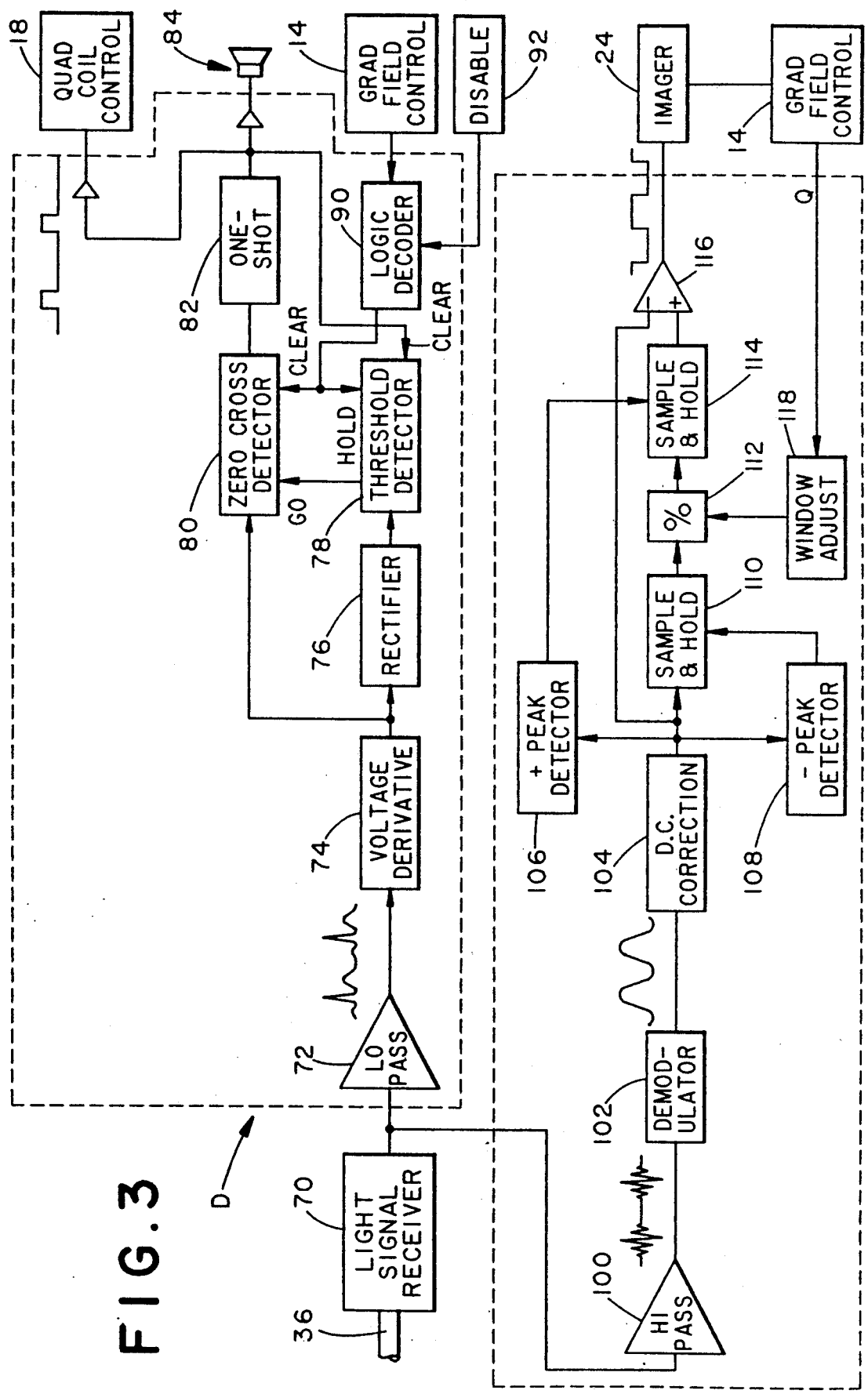
FIG. 3 is a circuit diagram of a light signal processing and magnetic resonance imager controlling portion of the present invention; and, FIG. 4 is a diagrammatic illustration of an alternate embodiment of the cardiac monitoring circuitry.

With particular reference to FIG. 3, a light signal receiver 70 receives the light signal from the fiber optic cable 36 and produces a corresponding received, combined data signal. A received signal separating means includes a low pass filter 72 for passing only signal components with the frequency on the order of the cardiac signal, i.e. separates the cardiac component of the received signal from other components. A 50 to 200 hertz low pass filter is preferred for separating cardiac data. Optionally, when monitoring other anatomical conditions, other signal separating means may be utilized.

A voltage derivative means 74 removes any DC offset introduced by the fiber optic link 36 and produces a voltage proportional to the change in voltage per unit time of the electrocardiogram signal. A rectifying means 76 rectifies the signal to produce a signal of the proper polarity for a threshold detector 78 to detect R-wave peaks of the cardiac cycle. The threshold detector 78 establishes a threshold level at two thirds of the previous R-wave peak derivative. Once the threshold has been exceeded a zero cross means 80 searches for the next occurence of zero crossing of the derivative signal. Comparing the derivative of the received cardiac signal with two thirds of the previous R-wave peak derivative locates the R-wave peak of the current cardiac signal. In this manner, variations in the derivative of the cardiac signals are automatically corrected.

A one shot multi-vibrator 82 generates a square wave trigger pulse of approximately 150 milliseconds in response to each R-wave peak. An audible indicator 84 provides an audible indication of each heart beat from the R-wave trigger pulse. The leading edge of each 150 millisecond trigger pulse is conveyed to the quadrature coil control means 18 to initiate the next scan.

In one mode of operation, the gradient field controller 14 produces a blanking signal as the gradient magnetic field is being applied. A blanking means blocks the initiation of the magnetic resonance imaging scan during application of the magnetic field gradient. In particular, a logic decoder 90 receives the signal indicative of a magnetic field gradient and blanks or otherwise prevents the threshold detector 78 from adjusting the threshold level and the zero-cross detector 80 form initiating a scan.

A disable means 92 selectively disables the logic decoder 90 or otherwise disables the blanking of the received signal during application of gradient magnetic fields. This enables the cardiac signal to be monitored even during the application of gradients. The monitoring of the cardiac signal even during the application of magnetic field gradients is of particular importance in cardiac imaging in which it is important or desirable to coordinate the phase of the cardiac cycle with the excitation or monitoring of resonance or the reconstruction of image representations.

The signal separating means further includes a respiratory or second anatomical condition separating means 100, such as a 700 hertz high pass filter, for separating the respiratory signal component from the cardiac and other components. A demodulator 102 demodulates the encoded carrier signal to produce a voltage which varies with the respiratory cycle. A DC correction means 104 establishes a zero level for subsequent peak detection.

A positive peak detector 106 and a negative peak detector 108 search for the respective extremes of the respiratory signal cycle. A first respiratory extreme, particularly the negative peak magnitude, is stored in a first or negative sample and hold circuit 110. A multiplier means 112 reduces the stored peak amplitude a preselected percentage, e.g. 70%. A second sample and hold circuit 114 stores the preselected percentage of the previous negative peak magnitude when enabled by the positive peak detector 106. This establishes a threshold for detecting the next rest period of the respiratory cycle.

A comparing means 116 compares the present respiratory signal amplitude with the threshold or window established in the second sample and hold 114. When the signal is less than the threshold, an enable or high signal is produced which allows scan data to be accepted and processed by the imager 24. When the received respiratory signal is greater than the threshold level, a blocking or data discard signal is generated which blocks the imager from accepting imaged data. This enable/blocking or window signal provides a window within which the received data may be processed.

Preferably, the window is slidably adjustable in order to optimize scan times. That is, limited amounts of data at the beginning of chest expansion and at the end of chest contraction may be processed with minimal degradation to the resultant image. At the beginning and ending of respiratory motion, the patient's chest is substantially at the quiescent stage. Rather than discarding any data in which the window signal is low during any portion of the scan data acquisition, the data may be retained if the signal remains low or turns low for only a small portion of the data receiving period. In some applications, it may be desirable to accelerate image data collection at the price of incorporating data scans collected during the limited respiratory movement. To this end, the window is selectively adjustable to permit either only data collected during the quiescent portions of the respiratory cycle or data collected in both quiescent and less quiescent portions of the respiratory cycle to be incorporated into the image.

In the preferred embodiment, the window is dynamically variable in accordance with the phase encoding of the view being acquired. Views with smaller phase angle encoding have a greater effect on the final image quality than views with higher phase angle encoding. The motion requirements are relaxed for the less sensitive, greater phase angle encoded views relative to the smaller angle encoded views.

A window adjusting means 118 selectively and dynamically increases and decreases the window as a function of the angle of phase encoding. For example, the multiplier means 112 may multiply the stored peak value by one of three preselected percentages depending upon whether the current view has smaller, greater, or intermediate phase encoding. Optionally, the window may be increased or decreased along a continuum in other increments, as other functions of the phase angle, or the like.

The dynamically varying window is of particular advantage in multi-slice data acquisition. The body's position is more likely to change between the collection of the first and last slice than during the acquisition of a single slice view. The dynamic window variation reduces the examination time by requiring little respiratory motion for smaller phase angle multi-slice views and relaxing the respiratory motion requirements as the phase angle increases.

Optionally, the window adjustment may also account for the breathing patterns of the patient. In particular, patients with long respiratory cycle repeat times are more likely to produce data which falls entirely during a quiescent period of the respiratory cycle than a patient with a shorter respiratory cycle. For a patient with a short respiratory cycle, a less stringent window quality may be necessary to produce an image in an acceptable duration of time.

Figure 4:
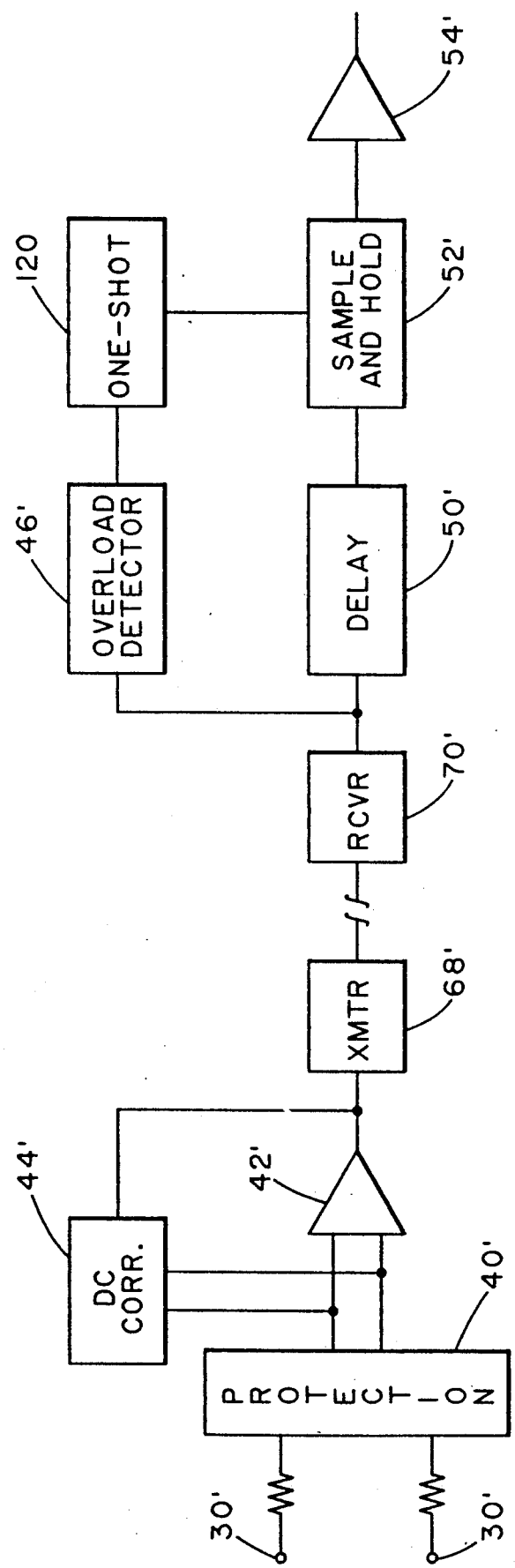

In the alternate embodiment of FIG. 4, like elements with the embodiment of FIGS. 2 and 3 are shown with like reference numerals but followed by a prime ('). The ECG signals are picked up by electrodes 30'. A protection circuit 40' insures that the patient does not receive shocks through the electrodes. An amplifier 42' amplifies the cardiac signals which are transmitted by a transmitting means 68' to a receiver 70' in a remote location. Changing electromagnetic fields in the neighborhood of the electrodes induces noise spikes which are superimposed on the ECG signals. The voltage spikes are not only shorter and more steeply sloped than the ECG signals but also have a higher amplitude. In the illustrated embodiment, the amplitude of the noise spikes is sufficiently great that it over loads or saturates the amplifier.

The noise detecting means includes an over load detector 46' which detects when a signal spike or component overloads the amplifier. Other amplitude discrimination means may also be utilized. Spikes which overload the amplifier or are in excess of a preselected amplitude maximum cause a resettable one-shot 120 to create a blanking pulse which has a duration that matches the normal duration of the noise spikes, e.g. 1 msec. In this manner, the output of the one shot is low except when a noise signal spike is detected.

A delay means 50' delays the superimposed noise and ECG signal such that the superimposed signal and the blanking signal from the one-shot arrive at a sample and hold circuit 52' concurrently. The sample and hold circuit functions as a track and hold means in that the received signal is provided as an output signal except when the sample and hold means is enabled by the blanking signal. In response to the blanking pulse from the one-shot 120, the sample and hold samples the received signal and holds its value constant until the end of the blanking pulse. Thereafter, the received signal is provided as the output signal. In this manner, the separating means separates noise spikes from the combined noise and ECG signal in response to the noise detecting means detecting the occurance of a noise spike or signal. More specifically, the separating means deletes the noise tainted signal segment and projects a replacement segment from the preceding signal segment. A low pass filter 54' smoothes the signal from the sample and hold circuit 52'.

The invention has been described with reference to the preferred embodiment. Obviously, modifications and alterations will occur to others upon reading and understanding the preceding specification. It is intended that the invention be construed as including all such alterations and modifications in so far as they come within the scope of the appended claims or the equivalents thereof.

Having thus described the preferred embodiment, the invention is now claimed to be:

1. An anatomical condition detecting apparatus for detecting an anatomical condition of a patient that is at least partially disposed in an examination region of a magnetic resonance diagnostic apparatus which generates a strong magnetic field and changes the magnetic field through the examination region, the anatomical condition detecting apparatus comprising:

an anatomical condition monitoring means for monitoring an anatomical condition and producing an anatomical condition electrical signal which varies in accordance therewith, the anatomical condition signal varying generally with a characteristic waveform having at least one preselected property, changing magnetic fields inducing noise which varies with a noise waveform that is superimposed on portions of the anatomical condition signal;

a magnetic field monitoring means for monitoring changes in the magnetic fields;

a separating means for deleting the superimposed noise from the anatomical condition signal in response to the monitored magnetic field changes.

2. An anatomical condition detecting apparatus for detecting an anatomical condition in a region of changing electromagnetic fields, the apparatus comprising:

an anatomical condition monitoring means for monitoring an anatomical condition and producing an anatomical condition electrical signal which varies in accordance therewith, the anatomical condition signal varying generally with a characteristic waveform having at least one preselected property, changing electromagnetic fields inducing noise which varies with a noise waveform superimposed on portions of the anatomical condition signal;

an electromagnetic field monitoring means for monitoring changes in the electromagnetic fields;

a separating means for deleting the superimposed noise waveform from the anatomical condition signal, the separating means including:

a track and hold means which in a first state supplies a received signal as an output signal and in a second state holds the output signal generally at an amplitude of the output signal when the second mode was entered, a comparing means for comparing the noise waveform with a preselected limit, the comparing means being connected with the track and hold means such that the comparing means switches the track and hold means between its first and second states.

3. The apparatus as set forth in claim 2 further including a filter means connected with the track and hold means for smoothing the output signal.

4. In a magnetic scanner for scanning a patient in an image region, a cardiac detector disposed adjacent the image region comprising:

a cardiac monitoring means for monitoring a patient's cardiac cycle, the cardiac monitoring means being disposed adjacent the image region for producing a cardiac signal indicative of the monitored patient cardiac cycle which cardiac signal conforms generally to a characteristic cardiac waveform, changing electromagnetic fields of the scanner inducing electrical noise spikes superimposed on the cardiac signal;

a detecting means for detecting occurrence of the changing magnetic fields that induce the noise spikes;

a means connected with the detecting means and the cardiac monitoring means for removing the noise spikes from the cardiac signal.

5. In a magnetic scanner for scanning a patient in an image region, a cardiac detector disposed adjacent the image region comprising:

a cardiac monitoring means for monitoring a patient's cardiac cycle, the cardiac monitoring means being disposed adjacent the image region, the cardiac monitoring means producing a cardiac signal indicative of the monitored patient's cardiac cycle, changing electromagnetic fields of the scanner inducing electrical noise signals that are superimposed on the cardiac signal;

an antenna disposed adjacent the image region for detecting the noise signals;

a separating means connected with the cardiac monitoring means and the antenna to receive the cardiac signal with superimposed noise and the noise signal, respectively, therefrom for separating the cardiac signal and the noise signal.

6. A method of monitoring an anatomical condition for a patient subject to changing magnetic fields, the method comprising:

connecting an anatomical condition monitor with the patient, which monitor produces an anatomical condition signal that varies in accordance with the monitored anatomical condition;

subjecting the patient to a strong magnetic field;

changing the magnetic field to which the patient is subject, the changing magnetic field inducing noise signals which are superimposed on the anatomical condition signal;

detecting the occurrence of the changes in the magnetic field;

separating the superimposed noise signals from the anatomical condition signal in response to the detected magnetic field changes.

7. The method as set forth in claim 6 wherein the detecting step includes measuring electrical signals induced by the changing magnetic field.

* * * * *